United States Patent [19]

Johansen

[11] 4,044,608
[45] Aug. 30, 1977

[54] METHOD FOR IN SITU DETERMINATION OF CONCRETE STRENGTH

[75] Inventor: Randulf Inge Johansen, Trondheim, Norway

[73] Assignee: A/S Trondhjems Nagle & Spigerfabrik, Trondheim, Norway

[21] Appl. No.: 689,984

[22] Filed: May 26, 1976

[30] Foreign Application Priority Data

June 5, 1975 Norway .................................. 751978

[51] Int. Cl.$^2$ .............................................. G01N 3/20
[52] U.S. Cl. ................................................... 73/88 C
[58] Field of Search ............... 73/88 C, 100, 87, 88 E

[56] References Cited
U.S. PATENT DOCUMENTS

| | | | |
|---|---|---|---|
| 69,737 | 10/1867 | Wood | 73/4 R |
| 368,508 | 8/1887 | Bishop | 16/109 UX |
| 3,595,071 | 7/1971 | Da Rocha | 73/88 E |

Primary Examiner—Jerry W. Myracle
Attorney, Agent, or Firm—Wenderoth, Lind & Ponack

[57] ABSTRACT

A method is provided for assessing the strength of a concrete structure by determining the flexural strength at a test section at the base of a concrete core projection established by disposing a tubular form element in the freshly poured and levelled concrete and removing the tubular form when the concrete has hardened sufficiently. A special load cell is inserted in the surface opening of the slit left in the concrete by the tubular form and the load cell activated to apply a recordable, gradually increasing force to the top of the core projection until rupture occurs at the base of the core projection. The flexural strength of the test section is then derived from recordings of the applied force at the moment of rupture.

3 Claims, 4 Drawing Figures

METHOD FOR IN SITU DETERMINATION OF CONCRETE STRENGTH

BACKGROUND OF THE INVENTION

This invention relates to a method for in situ determination of the concrete strength in concrete structures or parts thereof.

The concrete industry has for a long time requested a rapid and practical tool to evaluate the rate of hardening in a concrete structure itself, both in order to determine when forms can be removed safely, and to establish, the most favourable curing and production methods.

Today several methods are available for determination of the concrete strength in a structure:

1. Non-destructive methods (recoil hamer, ball indentor, Windsor Probe Test) measure the elastic properties in the surface zone of the concrete. These methods suffer from the drawback that they can only determine properties near the surface, and consequently they are strongly influenced by local disturbances (impurities and moisture content at the surface), and the fact that the elastic properties being measured have low correlation to conventional strength parameters.

2. Destructive methods are based on removal of specimens from the structure (by drilling out or by pre-set forms) and subsequent conventional testing in testing machines. All these methods are complicated, time-consuming and costly. Besides, drilling techniques cannot be used at low strength levels as the specimens will be damaged by the drilling load.

3. Semi-destructive methods are based on elements such as bolts or lugs embedded in the casting and measuring the force necessary to pull these elements out of the casting. These methods have the shortcomings that the stress condition and rupture zone at the moment of rupture are weakly defined. Further they are relatively complicated and time-consuming.

Up till now, in order to determine the strength properties in local zones differently spaced from the surface of the concrete, it has been necessary to remove specimens (by drilling, chiseling, etc.) which, after forming representative test pieces for the respective zones may be subjected to conventional strength testing.

SUMMARY OF THE INVENTION

The object of the invention is to provide a rapid and reliable method of assessing the strength characteristics of a concrete structure; to thereby secure safe stripping of formwork and economize and improve the production process.

Experience has shown that direct measurement of the concrete strength in the structure provides the most reliable registration of errors and defeciencies in the concrete production, whether they are caused by the composition of the mix, by the curing conditions or by the quality of the workmanship. The present invention utilizes such a test principle, as it is based on direct measurements of the flexural strength of the concrete in a plane located parallel to and at a certain distance from the concrete surface.

According to the invention in section to be investigated is established by means of form elements having tubular cross section and a certain length, which are placed in the formwork prior to casting or alternatively inserted into the freshly poured and levelled concrete. At the time of testing the element is removed thus leaving in the casting a slit surrounding a concrete core projection of geometry corresponding to the internal dimensions of the form element. The bending test is performed by applying a splitting force in the slit opening between the core projection and the surrounding concrete. Readings of the force are taken at the moment of rupture, (when the core cracks at the base) and the flexural strength of the concrete in the pertaining section may thus be determined.

The results from laboratory investigations and onsite tests have shown that the test principle according to the invention has numerous advantages compared to prior techniques:

The method is very suitable for the low strength levels of young concrete.

The method is very fast. It supplies an immediate, onsite answer to whether forms can be removed or not. The duration of the test, including insertion and removal of the tubular forms, is about 1 – 2 min. for each individual test.

The method is very simple and easy to operate. Normally, the concrete workers themselves may perform the required tests prior to stripping of formwork.

The method is applicable to vacuum concrete.

The test results are little influenced by reinforcement and concrete geometry, by the condition of the concrete surface or by temperature - and shrinkage forces.

The method is not dangerous in use, free of noise, and independent of access to electricity or water.

The correlation of the measurements of conventional compressive strength is satisfactory. This is considered an advantage as the existing technical experience concerning quality, design, construction and control, is closely linked to the use of the compressive strength as a strength criterion.

In addition to the application for control purposes, the method may be successfully used as a guide instrument for the production process. The measurements may then supply important information for a correct choice of concrete composition, admixture, curing time, heating system, covering, etc.

BRIEF DESCRIPTION OF THE DRAWINGS

An embodiment of the invention will now be described by way of example with reference to the accompanying drawings, in which.

DETAILED DESCRIPTION OF THE INVENTION

Figure 1A:
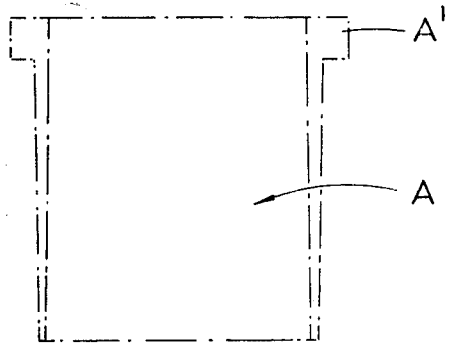
FIGS. 1a, 1b and 1c schematically illustrate the test principle of the process of the invention and apparatus for carrying out the same, FIG. 1a being a side view of a tabular form element according to the invention, FIG. 1b being a vertical section through the concrete structure in the test area, FIG. 1c being a plan and view of same area.
Figure 1B:
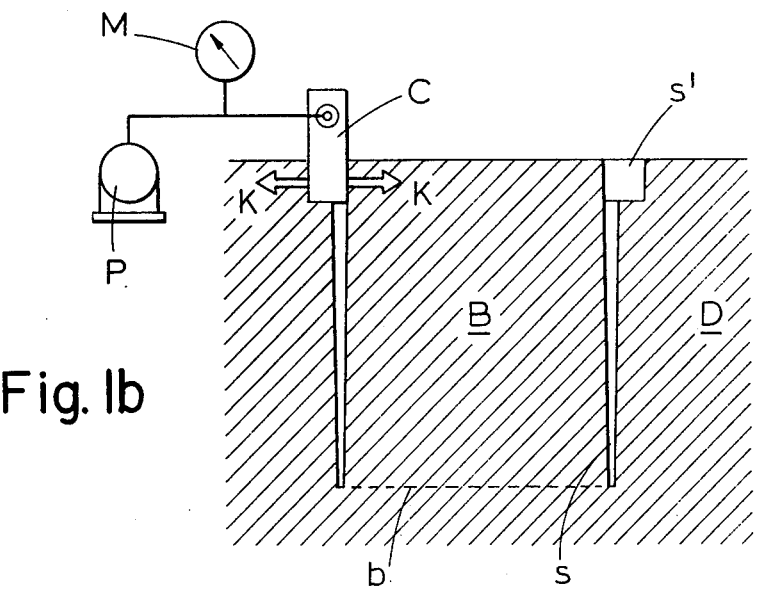

In FIG. 1b is shown the loading of a concrete core projection B formed by inserting a tubular form element A (indicated by dot-dash line in FIG. 1a ) into the freshly poured and levelled concrete casting D and withdrawing the form element when the concrete has hardened, leaving in the concrete a tubular slit s conformal to the form element A.

In the illustrated example the tubular form element has a circular or annular cross section. It should be emphasized however, that no principle requirements are made on the shape of the cross section of the form element which may have any convenient form such as circular, square, rectangular, etc., nor on the dimensions of the form element which thus may be selected from mere practical considerations.

As a practical example the cylindrical form element illustrated in FIG. 1a may have an internal diameter of about 55 mm. and a height of 70 mm. At its upper edge the element may have an outwardly extending circumferential rim portion A' of preferably rectangular cross section to produce a correspondingly outwardly extending recess s' on top of the slips s in the concrete D.

In order to facilitate removal of the form element A the tube wall thereof may be tapered from top to bottom, for instance by gradually reducing the outer diameter of the element. In the practical example mentioned above the thickness of the tube wall may taper from about 3 mm. just below the top rim A' down to about 1 mm. at the bottom of the element.

Figure 1C:
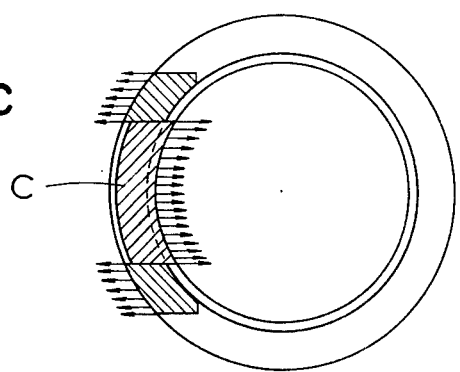

In the example illustrated in FIGS. 1b and 1c the testing force is applied by aid of a special oil pressure cell C which is accommodated in the extended recess S' on top of the slit s. The load cell C is activated by means of an ordinary hand operated hydraulic pump P to induce a lateral force K acting on the top side portion of the concrete core projection B and an equal reaction force acting on the opposite wall portion of recess s' in casting D, as indicated by arrows in FIG. 1b. The force required to cause rupture at base section b of the concrete core projection B is read off an ordinary pressure gauge, such as manometer M connected in the hydraulic line between pump P and load cell C and the corresponding flexural strength in that section may this be determined.

The weight of the test equipment described above will not exceed 5 kg., and the required time per test (placing a tube form element, removing this element and the test load) amounts to about two minutes. Thus, the method and apparatus according to the invention enables testing which is considerably simpler, faster and more economical than previously known methods. By using form elements of dissimilar height it is possible to obtain strength characteristics of the concrete at varying distances from the surface.

Figure 2:
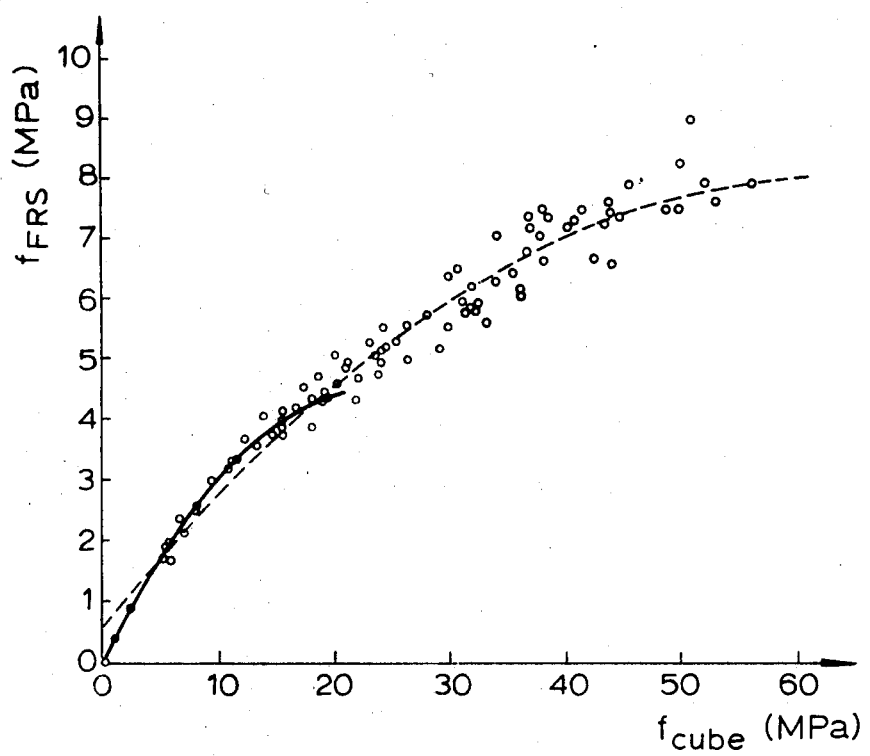
FIG. 2 is a diagram illustrating the correlation between flexural strength ($f_{FRS}$) as determined by means of the present method and equipment according to the invention and conventional compressive strength ($f_{cube}$) as determined on standard cube specimens.

In FIG. 2 test results of flexural strength ($f_{FRS}$) values as determined by the method according to the invention are plotted against corresponding conventionally obtained compression strength ($f_{cube}$) values and two ($f_{FRS}$) approximation curves are drawn to represent the correlation in the low strength region (solid curve) and the over-all strength region (broken curve) respectively, of the test.

The low strength correlation curve is given by the expression $$f_{FRS} = 0.381 f_{cube} - 0.00809 f_{cube}^2.$$

The corresponding correlation index is 0.991 with a standard error of estimate for $f_{FRS}$ and $f_{cube}$ of 0.18 MPa and 1.19 MPa, respectively.

The over-all strength correlation curve is given by the expression $$f_{FRS} = 0.57 + 0.233 f_{cube} - 0.00182 f_{cube}^2.$$

The corresponding correlation index is 0.980 with a standard error of estimate for $f_{FRS}$ and $f_{cube}$ of 0.37 MPa and 3,28 PMa, respectively.

I claim:

1. A method for in situ determination of concrete strength in a concrete structure or parts thereof, wherein the flexural strength of the concrete is determined at a test section located a certain distance from the surface of the concrete structure and preferably parallel thereto, said method comprising establishing the test section by arranging a tubular form element of a certain length in freshly poured and levelled concrete and extending down from the surface thereof, allowing the concrete to harden at least partly, removing the form element from the hardened or partly hardened concrete to leave in the concrete a slit surrounding a concrete core projection having a shape corresponding to the dimensions of the form element, and then subjecting the concrete core to a bending test by applying a recordable force at a place in the slit opening between the concrete core and the surrounding concrete until rupture occurs at the test section where the core is connected to the remaining concrete.

2. A method according to claim 1 wherein the tubular form element is arranged in a formwork of the concrete structure prior to pouring the concrete.

3. A method according to claim 1, wherein the tubular form element is inserted in the freshly poured and levelled concrete.

* * * * *